United States Patent [19]

Weithmann et al.

[11] Patent Number: 5,556,870
[45] Date of Patent: Sep. 17, 1996

[54] USE OF LEFLUNOMIDE FOR INHIBITING INTERLEUKIN 1 BETA

[75] Inventors: Klaus U. Weithmann, Hofheim; Robert R. Bartlett, Darmstadt, both of Germany

[73] Assignee: Hoechst Aktiengesellschaft, Frankfurt am Main, Germany

[21] Appl. No.: 411,849

[22] Filed: Mar. 28, 1995

Related U.S. Application Data

[63] Continuation of Ser. No. 177,960, Jan. 6, 1994, abandoned.

[30] Foreign Application Priority Data

Jan. 8, 1993 [DE] Germany .......................... 43 00 277.3

[51] Int. Cl.$^6$ .................................................. A61K 31/42
[52] U.S. Cl. .................................................. 514/378
[58] Field of Search .................................................. 514/378

[56] References Cited

U.S. PATENT DOCUMENTS

| 4,351,841 | 9/1982 | Kammerer et al. | 514/378 |
| 4,965,276 | 10/1990 | Bartlett et al. | 514/378 |

FOREIGN PATENT DOCUMENTS

| WO92/02822 | 2/1992 | WIPO . |
| WO92/16226 | 10/1992 | WIPO . |
| WO95/03297 | 2/1995 | WIPO . |

OTHER PUBLICATIONS

T. Zielinski et al., "Effects of Leflunomide (HWA 486) on Cell Cycle . . . ", Immunobiology, 186 (1–2):113 (1992).
T. Zielinski et al., "Effects of Leflunomide (HWA 486) on Expression . . . ", Agent Actions, 38 (1993).
T. Mattar et al., "Inhibition of the Epidermal Growth Factor Receptor . . . ", Fed. of European Biochemical Soc. 334(2):161–164 (1993).
T. T. Glant et al., "Immunomodulation of Proteoglycan–Induced Progressive Polyarthritis by Leflunomide", Immunopharmacology, 23:105–116 (1992).
R. R. Bartlett et al., "Leflunomide (HWA 486), a Novel Immunomodulating Compounds for the . . . ", Agents and Actions, 32 (½):10–21 (1991).
Chan, Rapid Communication, Inhibition of Tumor Necrosis Factor By Curcumin, A Phytochemcal, Biochemical Pharmacology, vol. 49, No. 11, pp. 1551–1556 (1995).

Primary Examiner—Jerome D. Goldberg
Attorney, Agent, or Firm—Finnegan, Henderson, Farabow, Garrett & Dunner, L.L.P.

[57] ABSTRACT

N-(4-Trifluoromethylphenyl)-5-methylisoxazole-4-carboxamide is an effective compound for preventing and treating disorders in which interleukin 1 beta is involved. It is used as a pharmaceutical.

1 Claim, No Drawings

USE OF LEFLUNOMIDE FOR INHIBITING INTERLEUKIN 1 BETA

This application is a continuation, of application Ser. No. 08/17,960, filed Jan. 6, 1994, now abandoned.

Leflunomide (see formula, N-(4-trifluoromethylphenyl)-5-methylisoxazole-4-carboxamide) is already known as a chemical compound (EP 0013376, EP 0217206, U.S. Pat. Nos. 4,351,841, 4,965,276).

In addition to its antiinflammatory effects, which have already been disclosed, this substance also brings about immunomodulatory effects which qualify it for use in the treatment of autoimmune diseases and transplant rejection reactions. It is also already known that this metabolite with the designation N-(4-trifluoromethylphenyl)-2-cyano-3-hydroxycrotonamide (see formula) is responsible for the therapeutic effects of leflunomide.

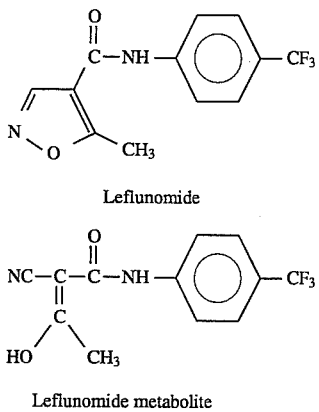

Leflunomide

Leflunomide metabolite

In correspondence with this finding, the pharmacological effects of leflunomide cited above can also be obtained by administering this said metabolite (Bartlett et al., Agents and Actions, 32 (1991) 10–21).

Axton et al., J. Chem. Soc. Perkin Trans. 1 (1992) 2203 ff. also describe how leflunomide does not represent the active principle and that, instead, this primary metabolite exhibits the biological effects.

It has been possible to demonstrate both in the literature (Bartlett et al., Agents and Actions, 32 (1991) 10–21) and in our own experiments that the therapeutic effects described in more detail below cannot be obtained by administering the leflunomide metabolite. Thus, it was found, in accordance with the invention, that leflunomide exerts a strong inhibitory effect on the synthesis and liberation of cytokines from human blood cells, whereas the leflunomide metabolite does not exhibit this advantageous effect.

Under the experimental conditions employed in accordance with the invention, no appreciable metabolism of leflunomide takes place, and the inhibitory effect is to be ascribed exclusively to the substance leflunomide.

The cytokines are a class of diverse, biologically highly potent, peptides whose structures are already known. It is likewise already known that they are induced and synthesized endogenously as transmitter substances.

The suppression of cytokines in the human or animal body is of great medical importance since excessive levels of these cytokines can lead to the occurrence or outbreak of numerous disorders.

Such disorders could be treated with a medicament which inhibits the undesirable effect of the cytokine, which might already be present, on the organ, cell, tissue and receptor systems of the body; however, it is now a further, significant advantage of the present invention that the use of leflunomide inhibits the actual synthesis and liberation of the cytokine so that the latter never even comes into being and the emergence of the disorder can thus be prevented at a very early phase.

The present invention relates to the use of leflunomide for preparing a pharmaceutical for preventing and treating disorders of the human and animal body in which the cytokine with the designation interleukin 1 beta (IL$\beta$) is involved.

The present invention also further relates to the use of leflunomide for treating such disorders.

The invention also relates to pharmaceuticals which contain an effective quantity of leflunomide in addition to pharmaceutically suitable and physiologically tolerated excipients, diluents and/or other active compounds and auxiliary substances.

The invention also relates to a process for preparing a pharmaceutical for preventing and treating disorders in which interleukin 1 beta is involved, wherein leflunomide is brought into a suitable preparation form together with pharmaceutically suitable and physiologically acceptable excipients and, where appropriate, further suitable active compounds, additives or auxiliary substances.

IL1$\beta$ and its disease-causing effects are described in detail in Ibelgaufts, Lexikon Zytokine (Cytokine Dictionary), Medikon Verlag, Munich 1992, and in the literature cited therein.

However, the undesirable effects of IL1$\beta$ are also referred to in WO 92/02822 and WO 91/155577, for example, as well as in Thornberry et al., Nature 356 (1992) 768–774, Cerretti et al., Science 256 (1992) 97–100 and Eastgate, Duff et al., Lancet September 24 (1988) 706–709. Tanaka et al., An. Letts 21 (1988) 169–181 described the central role of IL1$\beta$ in septic shock, leukemia and hepatitis.

In addition to this, IL1$\beta$ has a broad biological spectrum of pathogenic activity in association with, for example, muscle breakdown, HIV infection and disorders of brain metabolism, such as Alzheimer's disease.

IL1$\beta$ can be synthesized in many different cells, such as macrophages, fibroblasts, endothelial cells and lymphocytes; the synthesis is particularly active in peripheral monocytes. It is thus understandable that IL1$\beta$ occupies a central position in particularly serious disorders which can currently either not be treated at all or only treated inadequately. For this reason too, the effect of leflunomide which has been discovered is of great importance.

The present invention furthermore relates to the use of leflunomide for preventing and treating disorders involving increased cartilage resorption, meningitis, microbacterial infections, thromboses, arteriosclerotic depositions, an elevated fat level or joint destruction (Mustafa et al., J. Pediat., 115 (1989) pages 208–213; Kindler et al., Cell, 56 (1989) pages 731 ff., Joly et al., Circ. Res., 71 (1992) pages 331 ff. Ku et al., JBC, 267 (1992) page 14183; Chin et al., Arthritis and Rheumatism, 34 (1991) pages 314 ff.).

Pharmaceutical forms and pharmaceutical preparations of leflunomide, which have been prepared in the customary manner, can also, in particular, be used for treating these disorders.

Suitable solid or liquid pharmaceutical preparation forms are, for example, granules, powders, coated tablets, tablets, (micro)capsules, suppositories, syrups, juices, suspensions, emulsions, drops or injectable solutions, as well as preparations having a protracted release of active compound, in whose preparation customary adjuvants, such as excipients, disintegrants, binding agents, coating agents, swelling agents, glidants, lubricants, flavorants, sweeteners or solubilizers are used. Frequently used auxiliary substances which may be mentioned are, for example, magnesium carbonate, titanium dioxide, lactose, mannitol and other sugars, talc, milk protein, gelatin, starch, cellulose and its derivatives, animal and plant oils, polyethylene glycols, and solvents, such as, for example, sterile water and monohydric or polyhydric alcohols, e.g. glycerol.

In human medicine, dose units of 3 to 5 mg, preferably 10, 25 or 50 rag, per patient (70 kg body weight) are administered. If required medically, the dose unit can be increased to 100, 200 or 500 mg per patient. Dosing can take place once daily to once weekly, preferably up to three or four times daily. Administration can be effected orally, peritoneally, intravenously, intraarticularly or transdermally in a customary manner. The effective doses to be administered within veterinary medicine can also be readily calculated from these data.

Finally, in the preparation of the abovementioned pharmaceutical preparation forms, leflunomide can also be formulated together with other suitable active compounds, for example antiuricopathic agents, blood plateletaggregation inhibitors, analgesics, and other steroidal or non-steroidal antiinflammatory agents.

It was possible to demonstrate the effects of leflunomide experimentally on an isolated blood cell fraction (mononuclear cells), which cell fraction did not, to any appreciable extent, metabolize the leflunomide to its metabolites.

EXAMPLE 1

The mononuclear cells from freshly isolated human citrate blood were enriched in accordance with known standard procedures (see Tiku et al., J. Immunol. 136/10 (1986) 3677):

10 ml of freshly prepared human citrate blood were carefully underlaid with 15 ml of Lymphoprep® (Molter GmbH, Heidelberg) and then centrifuged at 400×g for 40 min. at 20° C. The cell fraction which was visible as a white ring at the phase boundary was withdrawn with the aid of a syringe, diluted 1:1 (v/v) with PM-16 buffer (from Serva Feinbiochemica GmbH & Co. KG, Heidelberg) and then centrifuged, as above, for 10 min. The supernatant was washed with 10 ml of RPMI 1640 buffer (Gibco, Berlin) to which 300 mg/l L-glutamine had previously been added. The washed cell fraction was taken up in 1 ml of RPMI 1640 to which 300 mg/l L-glutamine, 25 mmol/1 HEPES (Gibco, Berlin), 0.1 g/ml streptomycin and 0.1 g/ml penicillin had previously been added. Using a cell counter (type IT, from Coulter Diagnostics, Krefeld), the cell suspension, which is composed of about 90% lymphocytes and 10% monocytes, was adjusted to about 5 million cells/ml. Cell viability was monitored before and after the inhibition experiments using the known lactate dehydrogenase method. In this case, no change in viability was observed.

The synthesis and liberation of cellular IL1$\beta$ was induced by adding a solution of 500 ng of lipopolysaccharide (Salmonella abortus equi, Sigma GmbH, Deisenhofen) in 0.01 ml of dimethyl sulfoxide/water (1:10, v/v) to 0.48 ml of the above-described cell fraction. At the same time, a solution of leflunomide or leflunomide metabolite in 0.01 ml of dimethyl sulfoxide (for the final concentration in each case, see Tab. 1) was added to the cell fraction and the mixture was left at 37° C. for 20 h in a commercially available incubator. After cooling down to 0° C., the samples were centrifuged for 1 min. in a bench centrifuge and in each case 0.025 ml aliquots of the supernatant were examined for their IL1$\beta$ content using a "sandwich" enzyme-immuno test kit (from Biermann GmbH, Bad Nauheim) in accordance with the manufacturer's instructions. The control values were determined without the addition of leflunomide or metabolite and set at 100%. In particular, any possible influence of dimethyl sulfoxide on the IL1$\beta$ level was excluded by appropriate comparative measurements.

In addition, aliquots of the test sample containing leflunomide were removed in a time-dependent manner and tested for their content of leflunomide or leflunomide metabolite using the high pressure liquid chromatography (C-18 column 3.9×150 mm, Waters GmbH, Eschborn, eluent: 600 ml of methanol/350 ml of water/50 ml of tetrahydrofuran/1 ml of phosphoric acid; flow rate 0.7 ml/min. at 2000 pounds per square inch (psi); detection in the ultraviolet range at 273 nm). It was found that, under the conditions employed, leflunomide is metabolized only very slowly, with a half life of about 10 hours.

TABLE 1

| Substance under examination | Concentration in experiments mmol/l | IL1$\beta$ in the supernatant % +/− standard deviation | Number n = |
| --- | --- | --- | --- |
| Leflunomide | 0.1 | 17 +/− 4 | 6 |
|  | 0.05 | 27 +/− 6 | 3 |
|  | 0.01 | 70 +/− 8 | 6 |
|  | 0.005 | 68 | 2 |
|  | 0.0001 | 86 +/− 11 | 4 |
| Leflunomide metabolite | 0.1 | 99 +/− 12 | 3 |
|  | 0.01 | 100 +/− 3 | 4 |
| Without either | 0 | 100 |  |

The abovementioned experiments demonstrate that the leflunomide metabolite has practically no effect on the IL1$\beta$ level, whereas the IL1$\beta$ level is clearly lowered following the addition of leflunomide.

EXAMPLE 2

Preparation of N-(4-trifluoromethylphenyl)-5-methylisoxa-zole-4-carboxamide

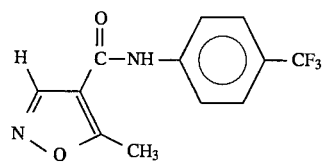

A solution of 0.05 mol of 4-methylisoxazole-4-carbonyl chloride (7.3 g) in 20 ml of acetonitrile is added dropwise, at room temperature, to a solution of 0.1 mol of 4-trifluoromethylaniline (16.1 g) in 150 ml of acetonitrile. After stirring for 20 minutes, the precipitated 4-trifluoromethylaniline hydrochloride is filtered off with suction and washed twice with 20 ml of acetonitrile on each occasion, and the combined filtrates are concentrated under reduced pressure. Yield: 12.8 g of white, crystalline N-(4-trifluoromethylphenyl)-5-methylisoxa-zole-4-catboxamide (leflunomide).

EXAMPLE 3

Acute toxicity following intraperitoneal administration

The acute toxicity following intraperitoneal administration of the test substance was carried out using NMRI mice (20 to 25 g) and SD rats (120 to 195 g). The test substance was suspended in a 1% strength solution of sodium carboxymethyl cellulose. The different doses of the test substance were administered to the mice in a volume of 10 ml/kg of body weight and to the rats in a volume of 5 ml/kg of body weight. 10 animals were used per dose. After 3 weeks, the acute toxicity was determined by the method of Litchfield and Wilcoxon. The results are summarized in Table 2.

TABLE 2

| | Leflunomide acute toxicity intraperitoneally $LD_{50}$ (mg/kg) |
|---|---|
| NMRI mouse | 185 (163–210) |
| SD rat | 170 (153–189) |

We claim:

1. A method for the treatment of a condition characterized by an elevated interleukin 1 beta level in a human or animal suffering from leukemia, hepatitis, increased cartilage absorption, HIV infection, Alzheimer's disease, muscle breakdown, meningitis, microbacterial infections, thromboses, arteriosclerotic depositions, or elevated fat level and joint destruction, wherein the method comprises administering to said human or animal N-(4-trifluoromethylphenyl)-5-methylisoxazole-4-carboxamide in an amount sufficient to inhibit the synthesis and liberation of said interleukin.

* * * * *